United States Patent
Bazin-Lee et al.

(10) Patent No.: US 10,882,876 B2
(45) Date of Patent: Jan. 5, 2021

(54) PEGYLATED IMIDAZOQUINOLINES AS TLR7 AND TLR8 AGONISTS

(71) Applicant: GlaxoSmithKline Biologicals SA, Rixensart (BE)

(72) Inventors: Helene G. Bazin-Lee, Hamilton, MT (US); David A. Johnson, Hamilton, MT (US)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 0 days.

(21) Appl. No.: 16/459,776

(22) Filed: Jul. 2, 2019

(65) Prior Publication Data

US 2019/0375772 A1    Dec. 12, 2019

Related U.S. Application Data

(62) Division of application No. 15/781,905, filed as application No. PCT/EP2016/080645 on Dec. 12, 2016, now Pat. No. 10,351,582.

(60) Provisional application No. 62/266,880, filed on Dec. 14, 2015.

(51) Int. Cl.
| | | |
|---|---|---|
| *C07F 9/6561* | (2006.01) | |
| *A61P 17/12* | (2006.01) | |
| *A61P 31/20* | (2006.01) | |
| *A61P 31/14* | (2006.01) | |
| *A61P 35/00* | (2006.01) | |

(52) U.S. Cl.
CPC ............ *C07F 9/6561* (2013.01); *A61P 17/12* (2018.01); *A61P 31/14* (2018.01); *A61P 31/20* (2018.01); *A61P 35/00* (2018.01)

(58) Field of Classification Search
CPC ................................ C07F 9/6561; A61P 31/20
See application file for complete search history.

(56) References Cited

U.S. PATENT DOCUMENTS

| 8,624,029 B2 | 1/2014 | Johnson |
| 8,946,421 B2 | 2/2015 | Johnson |
| 10,351,582 B2 * | 7/2019 | Bazin-Lee .............. A61P 17/12 |

FOREIGN PATENT DOCUMENTS

| EP | 2674170 A1 | 12/2013 |
| WO | 2010048520 A1 | 4/2010 |
| WO | 2012024284 A1 | 2/2012 |

OTHER PUBLICATIONS

Bazin, Helene G., et al. "Phospholipidation of TLR7/8-active imidazoquinolines using a tandem phosphoramidite method", Tetrahedron Letters, Elsevier, Amsterdam, NL, vol. 57, No. 19, Apr. 1, 2016 (Apr. 1, 2016), pp. 2063-2066.

Molineux, et al. "Pegylation: engineering improved pharmaceuticals for enhanced therapy", Cancer Treatment Reviews, Elsevier, Amsterdam, NL, vol. 28, Jan. 1, 2002 (Jan. 1, 2002), pp. 13-16.

Mwakwari, Sandra C et al. "Efficient tin-mediated synthesis of lysophospholipid conjugates of a TLR7/8-active imidazoquinoline", Tetrahedron Letters, Elsevier, Amsterdam, NL, vol. 57, No. 19, Apr. 1, 2016 (Apr. 1, 2016), pp. 2093-2096.

\* cited by examiner

*Primary Examiner* — Golam M Shameem
(74) *Attorney, Agent, or Firm* — Birch, Stewart, Kolasch & Birch, LLP

(57) ABSTRACT

The present invention provides novel phospholipidated imidazoquinolines as TLR7 and TLR8 agonists, pharmaceutical compositions, therapeutic uses and processes for preparing the same.

12 Claims, 3 Drawing Sheets

PEGYLATED IMIDAZOQUINOLINES AS TLR7 AND TLR8 AGONISTS

STATEMENT REGARDING FEDERALLY SPONSORED RESEARCH

This invention was made with Government support under contract #HHSN272200900036C awarded by the National Institutes of Health. The Government has certain rights in the invention.

BACKGROUND OF THE INVENTION

The present invention relates to toll-like receptor 7 (TLR7) and toll-like receptor 8 (TLR8) agonists. More particularly, the present invention relates to compounds useful as agonists for TLR7 and/or TLR8, compounds useful as adjuvants, methods of making such compounds, pharmaceutical formulations comprising such compounds, and therapeutic use of the same.

The refinement and simplification of microbial vaccines and the use of synthetic and recombinant subunit antigens to improve vaccine manufacturability and safety has resulted in a decrease in vaccine potency. This has led to studies on the co-administration of adjuvants with antigens to potentiate vaccine activity and the weak immunogenicity of synthetic and recombinant epitopes. Adjuvants are additives that enhance humoral and/or cell mediated immune responses to a vaccine antigen. The design of vaccine adjuvants, however, has historically been difficult because of the complex nature of the molecular mechanisms involved in immune system function. Although the addition of microbial components has long been known to enhance adaptive immune responses, only recently was it shown that toll-like receptors (TLRs) on cells involved in immune surveillance, such as epithelial and dendritic cells, engage many of these microbial products via so-called "pathogen-associated patterns" or PAMPs. Many vaccine adjuvants and stand-alone immunomodulators appear to interact with members of the TLR family.

Of the ten known TLRs that have been identified in humans, five are associated with the recognition of bacterial components (TLRs 1, 2, 4, 5, 6) and four others (TLRs 3, 7, 8, 9) appear to be restricted to cytoplasmic compartments and are involved in the detection of viral RNA (TLRs 3, 7, 8) and unmethylated DNA (TLR9) (Iwasaki, A., *Nat Immunol* 2004, 5, 987). Activation of TLRs regulates intracellular signaling pathways and leads to gene expression via interaction with intracellular adapter molecules such as MyD88, TRIF, TIRAP, and TRAM (Akira, S. *Nat Rev Immunol* 2004, 4, 499; Takeda, K. *Semin Immunol* 2004, 16, 3). These adapter molecules can differentially regulate the expression of inflammatory cytokines/chemokines and type I interferons (IFN-α,β), which can lead to the preferential enhancement of antigen-specific humoral and cell-mediated immune responses (Zughaier, S. *Infect Immun* 2005, 73, 2940). Humoral immunity is the major line of defense against bacterial pathogens, whereas the induction of cytotoxic T lymphocytes (CTLs) appears to be crucial for protective immunity in the case of viral disease and cancer.

Currently, a group of aluminum salts known as alum are the dominant adjuvants used in human vaccines. But alum typically only enhances humoral (Th2) immunity and is generally used intramuscularly due to local toxicity by other routes (e.g., subcutaneous or intradermal inoculation leads to granulomas) (Aguilar, J. *Vaccine* 2007, 25, 3752). Other potential side effects of alum include increased IgE production, allergenicity and neurotoxicity. Thus, new safe and effective vaccine adjuvants are needed which are able to stimulate both antibody and Th1-type immune responses and that are compatible with different routes of administration and antigen formulations.

In the case of TLR7 and TLR8 activation, a few different classes of small molecule mimetics of the natural (U- and/or G-rich) viral ssRNA ligands have been identified. These include certain antiviral compounds related to oxidized guanosine metabolites (oxoguanosines), which primarily interact with TLR7 (Heil, F. *Eur JImmunol* 2003, 33, 2987; Hemmi, 2002) and derivatives of adenine which engage TLR7 and/or TLR8. The immune stimulating ability of these compounds has been attributed to the TLR/MyD88-dependent signaling pathways and the production of cytokines, including IL-6 and type I (particularly interferon-α) and type II interferons. TLR7 or TLR8 activation leads to the upregulation of co-stimulatory molecules (e.g. CD-40, CD-80, CD-86) and class I and II MHC molecules on dendritic cells (DCs). DCs are the principal cells of the immune system involved in uptake and presentation of antigens to T lymphocytes. Plasmacytoid dendritic cells (pDCs), which preferentially express TLR7, are professional interferon-α producing cells; whereas myeloid dendritic cells (mDCs) express TLR8. TLR8 activation on mDCs leads to the preferential production of pro-inflammatory cytokines such as IL-12, TNF-α, and IFN-γ and cell-mediated immunity (CMI).

One class of adenine derivatives that has received a considerable amount of attention are the 1H-imidazo[4,5-c]quinolines (IQs). The prototypical member of this class imiquimod (R847, S-26398) was found to be effective against genital papilloma virus infections, actinic keratosis, and basal cell carcinoma when applied topically in cream form. However, imiquimod has relatively low interferon-inducing activity and both oral and topical preparations are not without side-effects. In fact, serious side effects were reported in an hepatitis C virus (HCV) clinical trial with imiquimod. The large immunological "footprint" of TLR7 agonists in general has led concerns over toxicity. Clinical trials with another TLR7 agonist ANA-975, an oxoguanosine derivative, were recently suspended due to toxicity issues.

As a first-line therapy for hepatitis C virus (HCV) disease, interferon combinations can be highly effective at reducing viral load and in some subjects in eliminating viral replication. However, many patients fail to show a sustained viral response and in these patients viral load is not controlled. Additionally, therapy with injected interferon may be associated with a number of unwanted adverse effects which are shown to affect compliance (Dudley T, O'Donnell K, Haydon G, Mutimer D. *Gut.*, 2006, 55 (9):1362-3). Administration of a small molecule compound which could stimulate the innate immune response, including the activation of type I interferons and other cytokines, could become an important strategy for the treatment or prevention of human diseases including viral infections. This type of immunomodulatory strategy has the potential to identify compounds which may be useful not only in infectious diseases but in cancer (Krieg. *Curr. Oncol. Rep.* 2004; 6 (2):88-95), allergic diseases (Moisan et al., *Am. J. Physiol. Lung Cell Mol. Physiol.* 2005; 290 (5):L987-95), other inflammatory conditions such as irritable bowel disease (Rakoff-Nahoum S., *Cell.* 2004, 23; 118 (2):229-41), and as vaccine adjuvants (Persing et al. *Trends Microbiol.* 2002; 10 (10 Suppl):S32-7).

Another member of the IQ class of TLR7/8 ligands and a derivative of a metabolite of imiquimod is resiquimod. Resiquimod (R-848, S-28609) also activates TLR7 in macrophages and DCs in a MyD88-dependent manner either directly or indirectly via an accessory molecule and upregulates co-stimulatory molecules and MHCI/II in DCs. But in contrast to imiquimod, the more potent and toxic resiquimod is also a ligand for TLR8 signaling, which leads to the reversal of CD4$^+$ regulatory (Treg) cell function. Using transfected HEK293 cells, it was recently shown that TLR7 agonists are more effective at generating IFN-α and IFN-regulated cytokines, whereas TLR8 agonists were more effective at inducing proinflammatory cytokines such as TNF-α and IL-12, suggesting that TLR7 activation may be more important for antibody responses (Th2-type responses) while TLR8 activation could drive CMI or Th1-type immune responses. However, as mentioned above, many TLR7/8 agonists often display toxic properties, are unstable, and/or have unsubstantial immunostimulatory effects. Thus, the discovery and development of effective and safe adjuvants that activate TLR7 and/or TLR8 is essential for improving the efficacy and safety of existing and new vaccines via helping to control the magnitude, direction, and duration of the immune response against antigens.

Unlike TLR2 and TLR4, which recognize PAMPs on cell surfaces, TLR7/8 PAMPs are sensed in the endosomal/lysosomal compartments and require endosomal maturation. Cellular uptake is prerequisite for cellular activation in the case of natural and zenobiotic TLR7/8 ligands such as imiquimod and resiquimod. Thus, strategies that would increase the penetration of the TLR7/8 ligand into DCs and other immune cells could enhance TLR activation and vaccine efficacy as well as ameliorate toxic effects.

The immune stimulating ability of certain antiviral/antitumor 1H-imidazo[4,5-c]quinolines (Gerster, J. F, et al. *J. Med. Chem.* 2005, 48, 3481-3491), such as imiquimod, has been attributed primarily to the activation of TLR7 in plasmacytoid dendritic cells and B cells and the induction of type I interferons (IFNα/β) and IFN-regulated cytokines (Miller, R. L.; Meng, T.-C.; Tomai, M. A. *Drug News Perspect.* 2008, 21, 69-87.).

TLR7/8 agonists in which an imidazoquinoline is conjugated to a phospho- or phosphonolipid have enhanced immune responses. It has been suggested that these agonists could improve immune responses due to direct intereaction of these compounds with endosomal TLR7 and/or TLR7/8 and/or interaction of an active metabolite after enzymatic action. (WO2010/04850).

SUMMARY OF THE INVENTION

As a first aspect, the present invention provides compounds of formula (I):

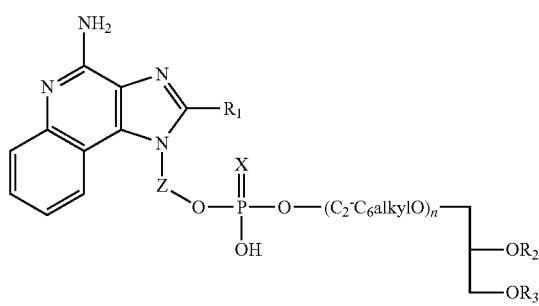

wherein $R_1$ is selected from H, $C_{1-6}$alkyl, $C_{1-6}$alkylamino, $C_{1-6}$alkoxy, $C_{3-6}$cycloalkylC$_{1-6}$alkyl, $C_{3-6}$cycloalkylC$_{1-6}$alkylamino, $C_{3-6}$cycloalkylC$_{1-6}$alkoxy, $C_{1-6}$alkoxyC$_{1-6}$alkyl, $C_{1-6}$alkoxyC$_{1-6}$alkylamino and $C_{1-6}$alkoxyC$_{1-6}$alkoxy; wherein the $C_{1-6}$alkyl, $C_{1-6}$alkylamino, $C_{1-6}$alkoxy, $C_{3-6}$cycloalkylC$_{1-6}$alkyl, $C_{3-6}$cycloalkylC$_{1-6}$alkylamino, $C_{3-6}$cycloalkylC$_{1-6}$alkoxy, $C_{1-6}$alkoxyC$_{1-6}$alkyl, $C_{1-6}$alkoxyC$_{1-6}$alkylamino or $C_{1-6}$alkoxyC$_{1-6}$alkoxy is branched or unbranched and optionally terminally substituted with a hydroxyl, amino, thio, hydrazino, hydrazido, azido, acetylenyl, carboxyl, or maleimido group;

Z is selected from $C_2$-$C_6$ alkyl and $C_2$-$C_6$ alkenyl, wherein the $C_2$-$C_6$ alkyl or $C_2$-$C_6$ alkenyl is unsubstituted or terminally substituted by —(O—$C_2$-$C_6$alkyl)$_{1-6}$—;

X is O or S;

n is 1, 2, 3, 4, 5, 6, 7, 8, 9, 10, 11, 12, 13, 14, 15, 16, 17, 18, 19 or 20;

$R_2$ is H or a straight or branched, optionally unsaturated, $C_4$-$C_{24}$ alkyl, or a straight or branched, optionally unsaturated, $C_4$-$C_{24}$, acyl;

$R_3$ is a straight or branched, optionally unsaturated, $C_4$-$C_{24}$ alkyl or a straight or branched, optionally unsaturated, $C_4$-$C_{24}$ acyl.

In a second aspect, the present invention provides a pharmaceutical composition comprising a compound of formula (I). The composition may further comprise a pharmaceutically acceptable carrier or diluent.

In a third aspect, the present invention provides a method for the treatment of a condition mediated by TLR7 and/or TLR8 activity in a subject in need thereof. The method comprises administering to the subject a therapeutically effective amount of a compound of formula (I).

In a fourth aspect, the present invention provides a method for the treatment of hepatitis C viral infection in a subject in need thereof. The method comprises administering to the subject a therapeutically effective amount of a compound of formula (I).

In a fifth aspect, the present invention provides a method for the treatment of basal cell carcinoma in a subject in need thereof. The method comprises administering to the subject a therapeutically effective amount of a compound of formula (I).

In a sixth aspect, the present invention provides a method for the treatment of actinic keratosis in a subject in need thereof. The method comprises administering to the subject a therapeutically effective amount of a compound of formula (I).

In a seventh aspect, the present invention provides a method for the treatment of genital papilloma viral infection in a subject in need thereof. The method comprises administering to the subject a therapeutically effective amount of a compound of formula (I).

In an eighth aspect, the present invention provides a method for use of a compound of formula (I) as a vaccine adjuvant.

In a ninth aspect, the present invention provides a process for preparing a compound of formula (I). This process comprises the steps of:

a) reacting a compound of formula (III)

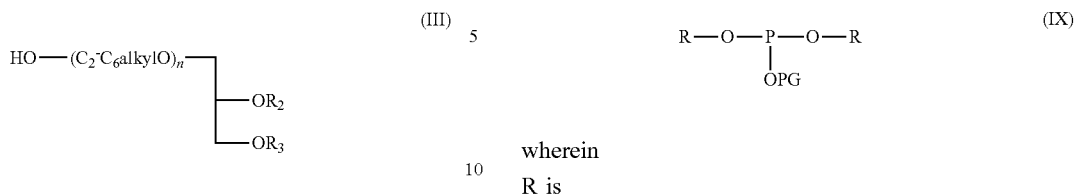
(III)

with a compound of formula (V)

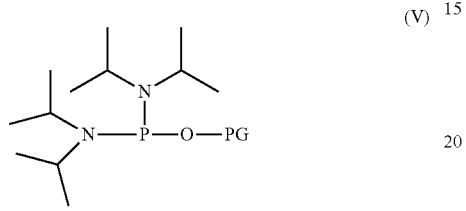
(V)

wherein PG is a protecting group suitable for hydroxyl protection, including but not limited to cyanoethyl, methyl, ethyl, benzyl and allyl group to prepare a compound of formula (VI)

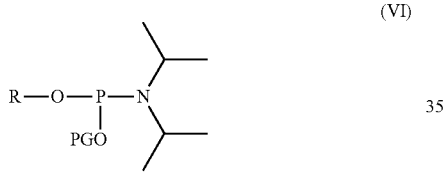
(VI)

wherein
R is

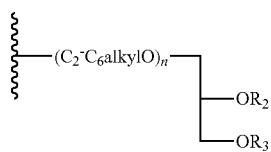

all other variables are as defined above for formula (I);

b) reacting a compound of formula (VI) with a compound of formula (VII)

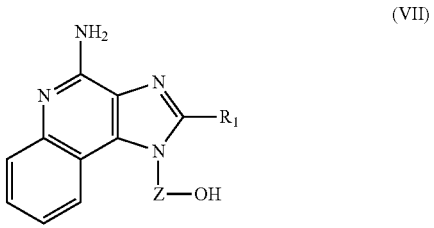
(VII)

to prepare a compound of formula (IX)

$$R-O-P-O-R$$
$$\underset{OPG}{|}$$
(IX)

wherein
R is

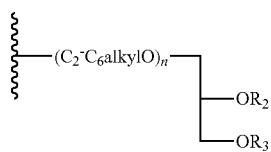

R' is

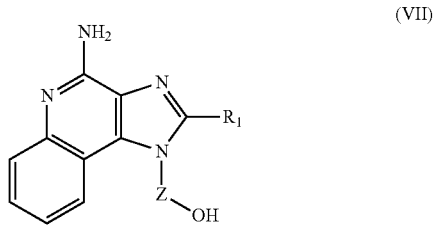

wherein PG is a protecting group suitable for hydroxyl protection, including but not limited to cyanoethyl, methyl, ethyl, benzyl and allyl group;

all other variables are as defined above for formula (I);

c) oxidizing a compound of formula (IX) and removing the hydroxyl protecting group to obtain a compound of formula (I);

d) optionally converting the compound of formula (I) into a pharmaceutically acceptable salt thereof;

e) optionally converting the compound of formula (I) into a different compound of formula (I).

In a tenth aspect, the present invention provides another process for preparing a compound of formula (I). This process comprises the steps of:

a) reacting a compound of formula (VII)

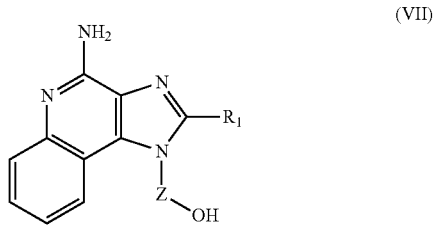
(VII)

with a H-phosphonate compound of formula (X)

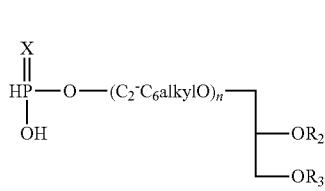

(X)

wherein all variables are as described above for formula (I) to prepare a compound of formula (I);

b) optionally converting the compound of formula (I) into a pharmaceutically acceptable salt thereof;

c) optionally converting the compound of formula (I) into a different compound of formula (I).

In another aspect, the present invention provides a compound of formula (I) for use in therapy. The present invention also provides a compound of formula (I) for use in the treatment of a condition mediated by TLR7 and/or TLR8 activity in a subject; a compound of formula (I) for use in the treatment of hepatitis C viral infection in a subject; a compound of formula (I) for use in the treatment of basal cell carcinoma in a subject; a compound of formula (I) for use in the treatment of actinic keratois in a subject; a compound of formula (I) for use in the treatment of genital papilloma viral infection in a subject; and a compound of formula (I) for use as a vaccine adjuvant.

In another aspect, the present invention provides the use of a compound of formula (I) for the preparation of a medicament for the treatment of a condition mediated by by TLR7 and/or TLR8 activity in a subject; the use of a compound of formula (I) for the preparation of a medicament for the treatment of hepatitis C viral infection; the use of a compound of formula (I) for the preparation of a medicament for the treatment of basal cell carcinoma; the use of a compound of formula (I) for the preparation of a medicament for the treatment of actinic keratosis in a subject; the use of a compound of formula (I) for the preparation of a medicament for the treatment of genital papilloma viral infection in a subject; and the use of a compound of formula (I) as a vaccine adjuvant for the preparation of adjuvanted vaccines.

In another aspect, the present invention provides a pharmaceutical composition comprising a compound of formula (I) for use in the treatment of a condition mediated by by TLR7 and/or TLR8 activity.

Further aspects of the present invention are described in the description of particular embodiments, examples, and claims which follow.

DETAILED DESCRIPTION OF THE PREFERRED EMBODIMENTS

Figure 1A:
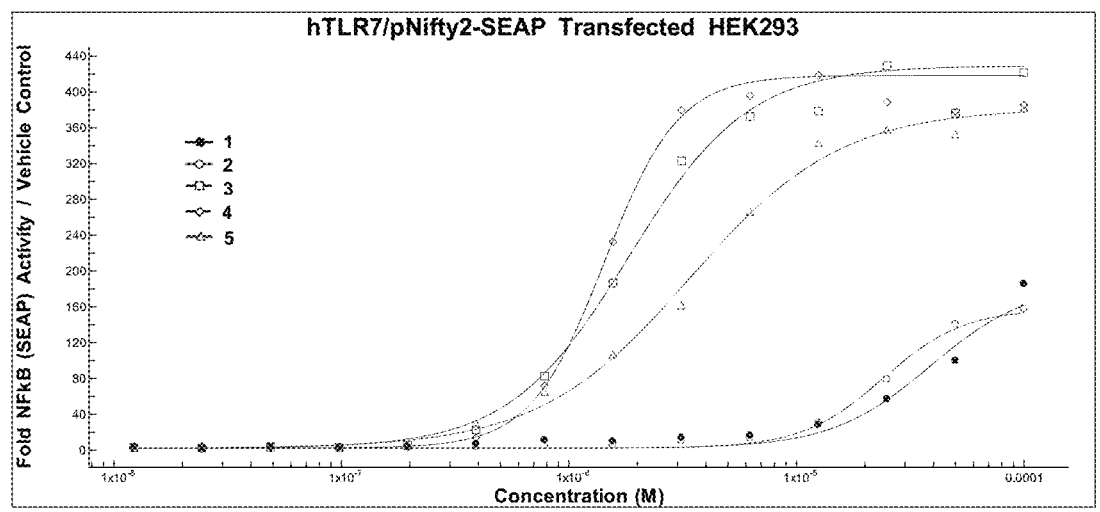
FIG. 1A and FIG. 1B: NFκB response of (A) HEK293-hTLR7 and (B) HEK293-hTLR8 cells treated for 24 hours with PEGylated analogs. Downstream signaling of hTLR7/8 receptors was monitored through NFκB mediated SEAP secretion. The activity profile of each compound was quantified through the measurement of SEAP activity in the HEK293 cell culture supernatant.
Figure 1:
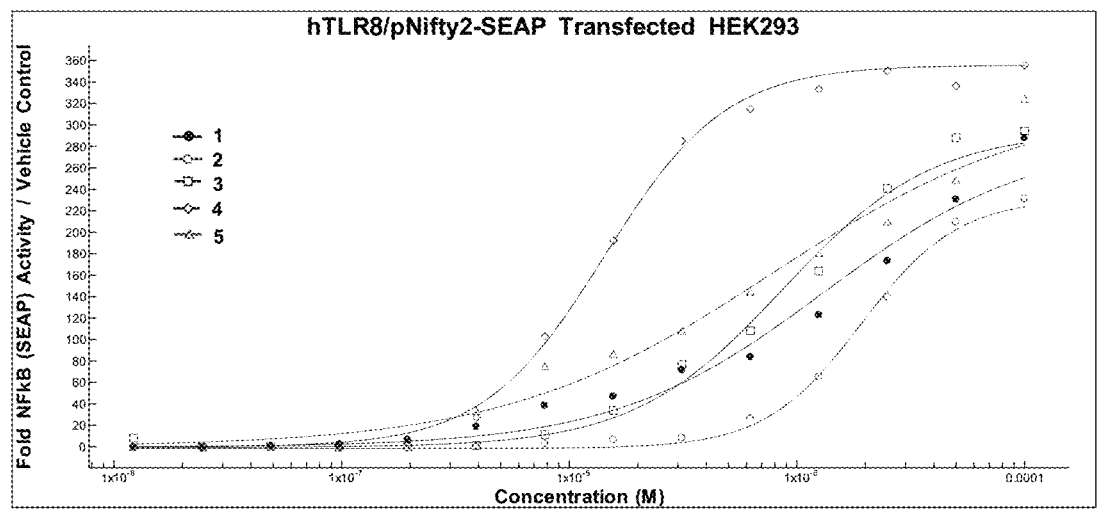
Figure 2:
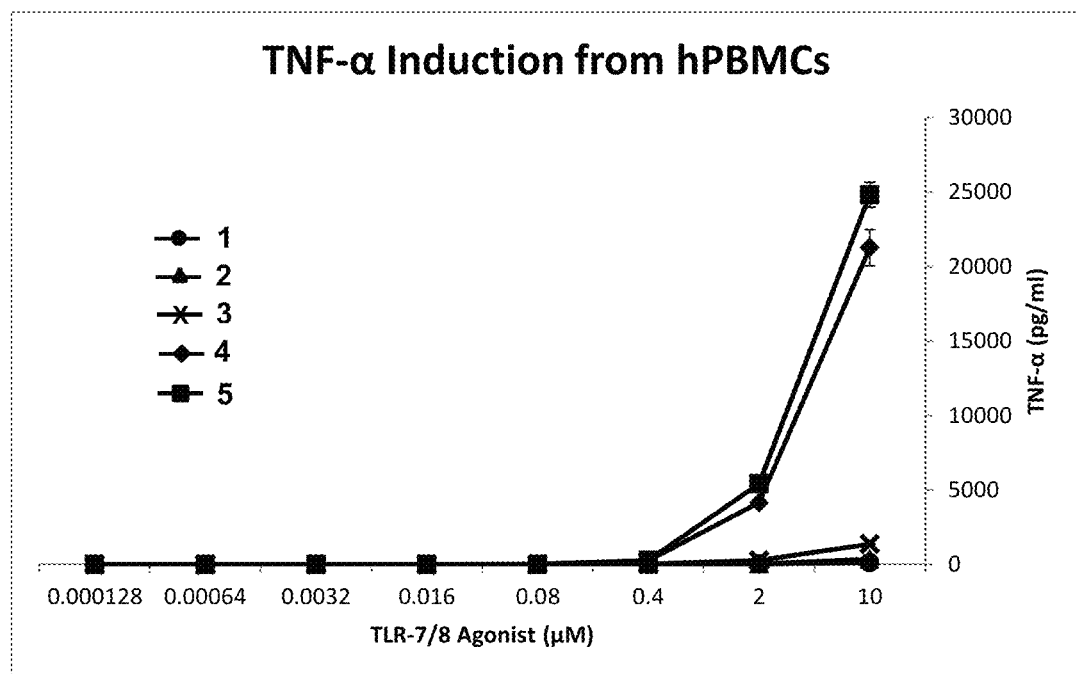
FIG. 2: TNF-α induction from hPBMCs by PEGylated imidazoquinolines.
Figure 3:
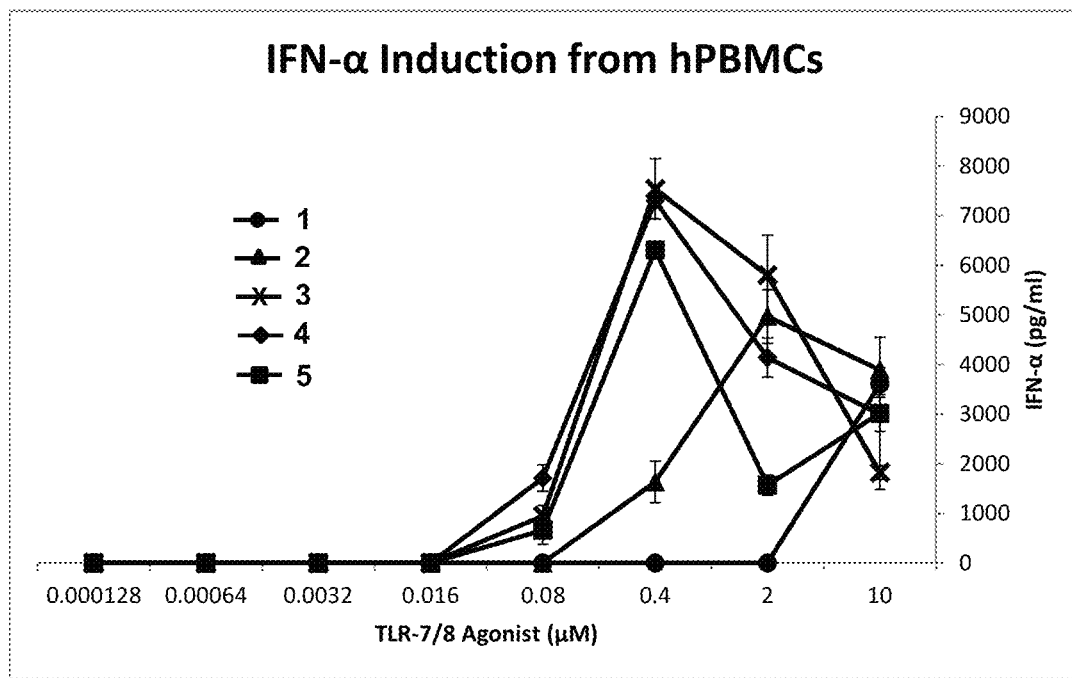
FIG. 3: IFN-α induction from hPBMCs by PEGylated imidazoquinolines.

As used herein, "a compound of the invention" or "a compound of formula (I)" means a compound of formula (I) or a pharmaceutically acceptable salt or solvate thereof.

The present invention provides compounds of formula (I):

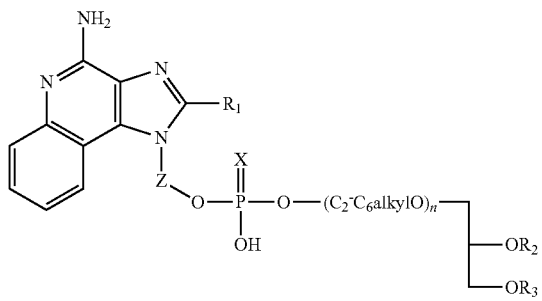

(I)

wherein $R_1$ is selected from H, $C_{1-6}$alkyl, $C_{1-6}$alkylamino, $C_{1-6}$alkoxy, $C_{3-6}$cycloalkyl$C_{1-6}$alkyl, $C_{3-6}$cycloalkyl$C_{1-6}$alkylamino, $C_{3-6}$cycloalkyl$C_{1-6}$alkoxy, $C_{1-6}$alkoxy$C_{1-6}$alkyl, $C_{1-6}$alkoxy$C_{1-6}$alkylamino and $C_{1-6}$alkoxy$C_{1-6}$alkoxy; wherein the $C_{1-6}$alkyl, $C_{1-6}$alkylamino, $C_{1-6}$alkoxy, $C_{3-6}$cycloalkyl$C_{1-6}$alkyl, $C_{3-6}$cycloalkyl$C_{1-6}$alkylamino, $C_{3-6}$cycloalkyl$C_{1-6}$alkoxy, $C_{1-6}$alkoxy$C_{1-6}$alkyl, $C_{1-6}$alkoxy$C_{1-6}$alkylamino or $C_{1-6}$alkoxy$C_{1-6}$alkoxy is branched or unbranched and optionally terminally substituted with a hydroxyl, amino, thio, hydrazino, hydrazido, azido, acetylenyl, carboxyl, or maleimido group;

Z is selected from $C_2$-$C_6$ alkyl and $C_2$-$C_6$ alkenyl, wherein the $C_2$-$C_6$ alkyl or $C_2$-$C_6$ alkenyl is unsubstituted or terminally substituted by —(O—$C_2$-$C_6$alkyl)$_{1-6}$-;

X is O or S;

n is 1, 2, 3, 4, 5, 6, 7, 8, 9, 10, 11, 12, 13, 14, 15, 16, 17, 18, 19 or 20;

$R_2$ is H or a straight or branched, optionally unsaturated, $C_4$-$C_{24}$ alkyl, or a straight or branched, optionally unsaturated, $C_4$-$C_{24}$, acyl;

$R_3$ is a straight or branched, optionally unsaturated, $C_4$-$C_{24}$ alkyl or a straight or branched, optionally unsaturated, $C_4$-$C_{24}$ acyl.

In one embodiment of the invention, $R_1$ is selected from H, $C_{1-6}$alkyl, $C_{1-6}$alkylamino and $C_{1-6}$alkoxy wherein the $C_{1-6}$alkyl, $C_{1-6}$alkylamino or $C_{1-6}$alkoxy is branched or unbranched and optionally terminally substituted with a hydroxyl, amino, thio, hydrazino, hydrazido, azido, acetylenyl, carboxyl, or maleimido group;

In one preferred embodiment, $R_1$ is $C_{1-6}$alkyl, e.g. $C_{1-4}$alkyl, such as butyl, particularly n-butyl.

In another preferred embodiment, Z is $C_2$-$C_6$ alkyl wherein the $C_2$-$C_6$ alkyl is unsubstituted or terminally substituted by —(O—$C_2$-$C_6$alkyl)$_{1-6}$-. In one such embodiment, Z is unsubstituted $C_2$-$C_6$ alkyl. In a preferred embodiment, Z is $(CH_2)_2$.

In another preferred embodiment X is O.

In another embodiment of the invention, n is 1, 2, 3, 4, 5, 6, 7, 8, 9, 10, 11 or 12.

In another embodiment, n is 3, 4, 5, 6, 7, 8, 9, 10, 11 or 12.

In another embodiment of the invention, n is 3, 4, 5, 6, 7, 8, or 9.

In another preferred embodiment, n is selected from 3, 6 and 9.

In another preferred embodiment, n is selected from 3 and 6.

In another preferred embodiment of the invention, n is 3.

In another preferred embodiment of the invention, n is 6.

In another preferred embodiment of the invention, n is 9.

In another embodiment of the invention, $R_2$ is a straight or branched, optionally unsaturated, $C_4$-$C_{24}$ acyl, e.g. a straight chain, saturated $C_4$-$C_{24}$ acyl, particularly $C_{10}$-$C_{20}$, such as $C_{16}$ acyl.

In another embodiment of the invention, $R_3$ is a a straight or branched, optionally unsaturated, $C_4$-$C_{24}$ acyl, e.g. a straight chain, saturated $C_4$-$C_{24}$ acyl, particularly $C_{10}$-$C_{20}$, such as $C_{16}$ acyl.

In one embodiment, $R_2$ and $R_3$ are the same. In an alternative embodiment, $R_2$ and $R_3$ are different.

In another preferred embodiment of the invention, $R_2$ is unbranched $C_{16}$ acyl (palmitoyl, $COC_{15}H_{31}$).

In another preferred embodiment of the invention, $R_3$ is is unbranched $C_{16}$ acyl (palmitoyl, $COC_{15}H_{31}$).

In another preferred embodiment of the invention, $R_2$ is H and $R_3$ is n-$C_{15}H_{31}CO$.

In a preferred embodiment of the invention, $R_1$ is $C_{1-6}$alkyl; Z is $C_2$-$C_6$ alkyl wherein the $C_2$-$C_6$ alkyl is unsubstituted or terminally substituted by —(O—$C_2$-$C_6$alkyl)$_{1-6}$-; X is O; n is 1, 2, 3, 4, 5, 6, 7, 8, 9, 10, 11 or 12; $R_2$ is a straight or branched, optionally unsaturated, $C_4$-$C_{24}$ acyl; and $R_3$ is a a straight or branched, optionally unsaturated, $C_4$-$C_{24}$ acyl.

In another preferred embodiment of the invention, $R_1$ is $C_{1-6}$alkyl; Z is unsubstituted $C_2$-$C_6$ alkenyl; X is O; n is 1, 2, 3, 4, 5, 6, 7, 8, 9, 10, 11 or 12; $R_2$ is a straight chain unsaturated, $C_4$-$C_{24}$ acyl; and $R_3$ is a straight chain, unsaturated, $C_4$-$C_{24}$ acyl.

In another preferred embodiment of the invention, $R_1$=n-butyl; Z is $(CH_2)_2$; n is selected from 3, 6 and 9; $R_2$ is $C_{16}$ acyl and $R_3$ is $C_{16}$ acyl.

Specific examples of particular compounds of the present invention are selected from the group consisting of:

4-amino-1-[2-(1,2-dipalmitoyl-sn-glycero-3-ethyleneglycol-phospho)ethyl]-2-n-butyl-1H-imidazo[4,5-c]quinoline;

4-amino-1-[2-(1,2-dipalmitoyl-sn-glycero-3-triethyleneglycol-phospho)ethyl]-2-n-butyl-1H-imidazo[4,5-c]quinoline;

4-amino-1-[2-(1,2-dipalmitoyl-sn-glycero-3-hexaethyleneglycol-phospho)ethyl]-2-n-butyl-1H-imidazo[4,5-c]quinoline;

4-amino-1-[2-(1,2-dipalmitoyl-sn-glycero-3-nonaaethyleneglycol-phospho)ethyl]-2-n-butyl-1H-imidazo[4,5-c]quinoline;

and pharmaceutically acceptable salts thereof.

One preferred compound of the invention is 4-amino-1-[2-(1,2-dipalmitoyl-sn-glycero-3-triethyleneglycol-phospho)ethyl]-2-n-butyl-1H-imidazo[4,5-c]quinoline; or a pharmaceutically acceptable salt thereof. In one particular embodiment, 4-amino-1-[2-(1,2-dipalmitoyl-sn-glycero-3-triethyleneglycol-phospho)ethyl]-2-n-butyl-1H-imidazo[4,5-c]quinoline; or pharmaceutically acceptable salt thereof is in crystalline form. In another embodiment, 4-amino-1-[2-(1,2-dipalmitoyl-sn-glycero-3-triethyleneglycol-phospho)ethyl]-2-n-butyl-1H-imidazo[4,5-c]quinoline is in the form of a choline salt.

Another preferred compound of the invention is 4-amino-1-[2-(1,2-dipalmitoyl-sn-glycero-3-hexaethyleneglycol-phospho)ethyl]-2-n-butyl-1H-imidazo[4,5-c]quinoline; or a pharmaceutically acceptable salt thereof. In one particular embodiment, 4-amino-1-[2-(1,2-dipalmitoyl-sn-glycero-3-hexaethyleneglycol-phospho)ethyl]-2-n-butyl-1H-imidazo[4,5-c]quinoline; or pharmaceutically acceptable salt thereof is in crystalline form. In another embodiment, 4-amino-1-[2-(1,2-dipalmitoyl-sn-glycero-3-hexaethyleneglycol-phospho)ethyl]-2-n-butyl-1H-imidazo[4,5-c]quinoline is in the form of a choline salt.

Certain compounds of formula (I) may exist in stereoisomeric forms (e.g. they may contain one or more asymmetric carbon atoms). The individual stereoisomers (enantiomers and diastereomers) and mixtures of these are included within the scope of the present invention. The present invention also covers the individual isomers of the compounds represented by formula (I) as mixtures with isomers thereof in which one or more chiral centers are inverted.

Suitable pharmaceutically acceptable salts according to the present invention will be readily determined by one skilled in the art and will include, for example, salts prepared from organic or inorganic bases such as lithium hydroxide, sodium hydroxide, potassium hydroxide, lithium carbonate, lithium hydrogen carbonate, sodium carbonate, sodium hydrogen carbonate, potassium carbonate, potassium hydrogen carbonate, as well as potassium tert-butoxide and organic bases such as diethyl amine, lysine, arginine, choline, tris (hydroxymethyl) aminomethane (tromethamine), triethanolamine, diethanolamine, and ethanolamine.

When used in medicine, the salts of a compound of formula (I) should be pharmaceutically acceptable, but pharmaceutically unacceptable salts may conveniently be used to prepare the corresponding free base or pharmaceutically acceptable salts thereof.

As used herein, the term "solvate" refers to a crystal form containing the compound of formula (I) or a pharmaceutically acceptable salt thereof and either a stoichiometric or a non-stoichiometric amount of a solvent. Solvents, by way of example, include water (thus producing hydrates), methanol, ethanol, or acetic acid. Hereinafter, reference to a compound of formula (I) is to any physical form of that compound, unless a particular form, salt or solvate thereof is specified.

Processes for preparing pharmaceutically acceptable salts of the compounds of formula (I) are conventional in the art. See, e.g., Burger's Medicinal Chemistry And Drug Discovery 5th Edition, Vol 1: Principles And Practice.

The compounds of the invention of formula (I) may be in crystalline or amorphous form.

Furthermore, some of the crystalline forms of the compounds of the invention may exist as polymorphs, all of which are included within the scope of the present invention. The most thermodynamically stable polymorphic form or forms of the compounds of the invention are of particular interest.

Polymorphic forms of compounds of the invention may be characterised and differentiated using a number of conventional analytical techniques, including, but not limited to, X-ray powder diffraction (XRPD), infrared spectroscopy (IR), Raman spectroscopy, differential scanning calorimetry (DSC), thermogravimetric analysis (TGA) and solid-state nuclear magnetic resonance (ssNMR).

It will be appreciated from the foregoing that included within the scope of the invention are hydrates, isomers and polymorphic forms of the compounds of formula (I) and salts thereof.

As will be apparent to those skilled in the art, in the processes described below for the preparation of compounds of formula (I), certain intermediates, may be in the form of pharmaceutically acceptable salts of the compound. Those terms as applied to any intermediate employed in the process of preparing compounds of formula (I) have the same meanings as noted above with respect to compounds of formula (I). Processes for preparing pharmaceutically acceptable salts of such intermediates are known in the art and are analogous to the process for preparing pharmaceutically acceptable salts of the compounds of formula (I).

In one embodiment, the compounds of formula (I) are TLR7 and/or TLR8 agonists. As used herein, the term "agonist" refers to compounds which exhibits TLR7 and/or TLR8 activity in the HEK 293 Assay described below and/or induces IFN-α and/or TNF-α in the Cytokine Induction Assay described below.

Compounds of formula (I) are useful in therapy in subjects such as mammals, and particularly humans. In particular, the compounds of formula (I) are useful in the treatment of a condition mediated by TLR7 and/or TLR8 activity in a subject such as a mammal, particularly a human. As used herein, the term "treatment" includes the prevention of occurrence of symptoms of the condition or disease in the subject, the prevention of recurrence of symptoms of the condition or disease in the subject, the delay of recurrence of symptoms of the condition or disease in the subject, the decrease in severity or frequency of outward symptoms of the condition or disease in the subject, slowing or eliminating the progression of the condition and the partial or total elimination of symptoms of the disease or condition in the subject.

The compounds of the invention induce interferon-α, TNF-α, IL-12 and other immunostimulatory cytokines. The amplitude of cytokine induction is modulated by the length of the PEGylated moiety. These compounds may possess an improved activity-toxicity profile in comparison to known cytokine inducers when used as adjuvants for vaccine antigens in the therapeutic or prophylactic treatment of infectious diseases and cancer.

Conditions which may be mediated by TLR7 activity and/or TLR8 and/or IFN-α include but are not limited to, inflammation, including but not limited to inflammatory or allergic diseases such as asthma, allergic rhinitis, hypersensitivity lung diseases, eosinophilic pneumonitis, delayed-type hypersensitivity, atherosclerosis, pancreatitis, gastritis, osteoarthritis, psoriasis, sarcoidosis, pulmonary fibrosis, respiratory distress syndrome, bronchiolitis, chronic obstructive pulmonary disease, sinusitis, cystic fibrosis, and dermatitis; autoimmune diseases including but not limited to rheumatoid arthritis, psoriatic arthritis, systemic lupus erythematosus, Sjöegrens disease, ankylosing spondylitis, scleroderma, diabetes, graft rejection, including graft-versus-host disease, inflammatory bowel diseases including, but not limited to, Crohn's disease and ulcerative colitis; infectious diseases including, but not limited to, those caused by hepatitis viruses (e.g. hepatitis B virus, hepatitis C virus), human immunodeficiency virus, papillomaviruses, herpesviruses, respiratory viruses (e.g. influenza viruses, respiratory syncytial virus, rhinovirus, metapneumovirus, parainfluenzavirus, SARS), and West Nile virus; microbial infections caused by, for example, bacteria, fungi, or protozoa including, but not limited to, tuberculosis, bacterial pneumonia, aspergillosis, histoplasmosis, candidosis, pneumocystosis, leprosy, chlamydia, cryptococcal disease, cryptosporidosis, toxoplasmosis, leishmania, malaria, and trypanosomiasis; various cancers, in particular the treatment of cancers that are known to be responsive to immunotherapy and including, but not limited to, renal cell carcinoma, lung cancer, breast cancer, colorectal cancer, bladder cancer, melanoma, leukaemia, lymphomas and ovarian cancer; basal cell carcinoma; actinic keratosis; genital papilloma viral infections; and liver regeneration. various cancers, in particular the treatment of cancers that are known to be responsive to immunotherapy and including, but not limited to, renal cell carcinoma, lung cancer, breast cancer, colorectal cancer, bladder cancer, melanoma, leukaemia, lymphomas and ovarian cancer; basal cell carcinoma; actinic keratosis; genital papilloma viral infections; and liver regeneration.

It will be appreciated by those skilled in the art that references herein to treatment or therapy extend to prophylaxis as well as the treatment of established conditions.

As described herein, compounds of the invention may be useful as therapeutic agents.

Compounds of formula (I) are believed to be useful for the treatment of hepatitis C viral infection in a subject, such as a mammal, particularly a human.

Compounds of formula (I) are believed to be useful for the treatment of basal cell carcinoma in a subject, such as a mammal, particularly a human.

By treating dyslipidemia, compounds of formula (I) are currently believed to be useful in the treatment of actinic keratosis in a subject such as a mammal, particularly a human.

The compounds of formula (I) are useful for the treatment of genial papilloma viral infection in a subject, such as a mammal, particularly a human.

The compounds of formula (I) are useful as a vaccine adjuvent in a subject, such as a mammal, particularly a human.

The present invention provides a method for the treatment of hepatitis C viral infection in a subject, such as a mammal, particularly a human, in need thereof. The present invention also provides the use of a compound of formula (I) for the preparation of a medicament for the treatment of hepatitis C viral infection in a subject. In one embodiment, the compound of formula (I) is 4-amino-1-[2-(1,2-dipalmitoyl-sn-glycero-3-triethyleneglycol-phospho)ethyl]-2-n-butyl-1H-imidazo[4,5-c]quinoline or a pharmaceutically acceptable salt thereof. In another embodiment, the compound of formula (I) is 4-amino-1-[2-(1,2-dipalmitoyl-sn-glycero-3-hexaethyleneglycol-phospho)ethyl]-2-n-butyl-1H-imidazo [4,5-c]quinoline or a pharmaceutically acceptable salt thereof.

The present invention provides a method for the treatment of basal cell carcinoma in a subject, such as a mammal, particularly a human, in need thereof. The present invention also provides the use of a compound of formula (I) for the preparation of a medicament for the treatment of basal cell carcinoma in a subject. In one embodiment, the compound of formula (I) is 4-amino-1-[2-(1,2-dipalmitoyl-sn-glycero-3-triethyleneglycol-phospho)ethyl]-2-n-butyl-1H-imidazo [4,5-c]quinoline or a pharmaceutically acceptable salt thereof. In another embodiment, the compound of formula (I) is 4-amino-1-[2-(1,2-dipalmitoyl-sn-glycero-3-hexaethyleneglycol-phospho)ethyl]-2-n-butyl-1H-imidazo[4,5-c] quinoline or a pharmaceutically acceptable salt thereof.

The present invention provides a method for the treatment of actinic keratosis in a subject, such as a mammal, particularly a human, in need thereof. The present invention also provides the use of a compound of formula (I) for the preparation of a medicament for the treatment of actinic keratosis in a subject. In one embodiment, the compound of formula (I) is 4-amino-1-[2-(1,2-dipalmitoyl-sn-glycero-3-triethyleneglycol-phospho)ethyl]-2-n-butyl-1H-imidazo[4, 5-c]quinoline or a pharmaceutically acceptable salt thereof. In another embodiment, the compound of formula (I) is -amino-1-[2-(1,2-dipalmitoyl-sn-glycero-3-hexaethyleneglycol-phospho)ethyl]-2-n-butyl-1H-imidazo[4,5-c]quinoline or a pharmaceutically acceptable salt thereof.

The present invention provides a method for the treatment of genial papilloma viral infections in a subject, such as a mammal, particularly a human, in need thereof. The present invention also provides the use of a compound of formula (I) for the preparation of a medicament for the treatment of genial papilloma viral infections in a subject. In one embodiment, the compound of formula (I) is 4-amino-1-[2-(1,2-dipalmitoyl-sn-glycero-3-triethyleneglycol-phospho)ethyl]-2-n-butyl-1H-imidazo[4,5-c]quinoline or a pharmaceutically acceptable salt thereof. In another embodiment, the compound of formula (I) is -amino-1-[2-(1,2-dipalmitoyl-sn-glycero-3-hexaethyleneglycol-phospho) ethyl]-2-n-butyl-1H-imidazo[4,5-c]quinoline or a pharmaceutically acceptable salt thereof.

The present invention also provides the use of a compound of formula (I) as a vaccine adjuvant in a subject, such as a mammal, particularly a human, in need thereof. In one embodiment, the compound of formula (I) is 4-amino-1-[2-(1,2-dipalmitoyl-sn-glycero-3-triethyleneglycol-phospho) ethyl]-2-n-butyl-1H-imidazo[4,5-c]quinoline or a pharmaceutically acceptable salt thereof. In another embodiment, the compound of formula (I) is -amino-1-[2-(1,2-dipalmitoyl-sn-glycero-3-hexaethyleneglycol-phospho)ethyl]-2-n-butyl-1H-imidazo[4,5-c]quinoline or a pharmaceutically acceptable salt thereof.

All of the methods of the present invention comprise the step of administering a therapeutically effective amount of the compound of formula (I). As used herein, the term "therapeutically effective amount" refers to an amount of a compound of formula (I) which is sufficient to achieve the stated effect in the subject to which it is administered. Accordingly, a therapeutically effective amount of a compound of formula (I) used in the method for the treatment of a condition mediated by TLR7 and/or TLR8 activity in a human will be an amount sufficient for the treatment of the condition mediated by TLR7 and/or TLR8 activity in a human. A therapeutically effective amount of a compound of formula (I) for use in the method for the treatment of hepatitis C viral infection in a human will be an amount sufficient for the treatment of hepatitis C viral infection in a human. A therapeutically effective amount of a compound of formula (I) for use in the method for the treatment of basal cell carcinoma in a human will be an amount sufficient for the treatment of basal cell carcinoma in a human. A therapeutically effective amount of a compound of formula (I) for use in the method for the treatment of actinic keratosis in a human will be an amount sufficient for the treatment of actinic keratosis in a human. A therapeutically effective amount of a compound of formula (I) for use in the method for the treatment of genital papilloma viral infection in a human will be an amount sufficient for the treatment of genital papilloma viral infection in a human.

The amount of a compound of formula (I) which is required to achieve the desired therapeutic or biological effect will depend on a number of factors such as the use for which it is intended, the means of administration, the recipient and the type and severity of the condition or disease being treated, and will be ultimately at the discretion of the attendant physician or veterinarian. This dose may be administered as a single unit dose or as several separate unit doses or as a continuous infusion. Similar dosages would be applicable for the treatment of other diseases, conditions and therapies in humans.

While it is possible that, for use in therapy, a therapeutically effective amount of a compound of formula (I) may be administered as the raw chemical, it is typically presented as the active ingredient of a pharmaceutical composition or formulation. Accordingly, the invention further provides a pharmaceutical composition comprising a compound of the formula (I). The pharmaceutical composition may further comprise one or more pharmaceutically acceptable carriers or diluents. The carrier(s) and/or diluent(s) must be acceptable in the sense of being compatible with the other ingredients of the formulation and not deleterious to the recipient thereof. In one particular embodiment, the compound is in crystalline form. In accordance with another aspect of the invention there is also provided a process for the preparation of a pharmaceutical formulation including admixing a compound of the formula (I) with one or more pharmaceutically acceptable carriers and/or diluents.

Pharmaceutical formulations may be presented in unit dose form containing a predetermined amount of active ingredient per unit dose. Such a unit may contain a therapeutically effective dose of the compound of formula (I) or a fraction of a therapeutically effective dose such that multiple unit dosage forms might be administered at a given time to achieve the desired therapeutically effective dose. Preferred unit dosage formulations are those containing a daily dose or sub-dose, as herein above recited, or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethyl-cellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of active ingredient. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax or the like.

A compound of formula (I) can also be administered in the form of liposome delivery systems, such as small unilamellar vesicles, large unilamellar vesicles and multilamellar vesicles. Liposomes can be formed from a variety of lipids, such as cholesterol, stearylamine or phospholipids such as phosphatidylcholines.

A compound of formula (I) can also be administered in the form of nanoparticle delivery systems, such as solid lipid nanoparticles or microspheres.

A compound of of formula (I) can also be administered as an emulsion delivery system, such as an oil in water emulsion.

A compound of formula (I) may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis as generally described in 1986 Pharmaceutical Research 3:318.

Pharmaceutical compositions adapted for topical administration may be formulated as ointments, creams, suspensions, lotions, powders, solutions, pastes, gels, sprays, aerosols or oils.

For treatments of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent.

Pharmaceutical compositions adapted for topical administration in the mouth include lozenges, pastilles and mouth washes.

Pharmaceutical compositions adapted for rectal administration may be presented as suppositories or as enemas.

Pharmaceutical compositions adapted for nasal administration wherein the carrier is a solid include a coarse powder having a particle size for example in the range of about 20 microns to about 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical compositions adapted for administration by inhalation include fine particle dusts or mists, which may be generated by means of various types of metered, dose pressurised aerosols, nebulizers or insufflators.

Pharmaceutical compositions adapted for vaginal administration may be presented as pessaries, tampons, creams, gels, pastes, foams or spray formulations.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the compositions may include other agents conventional in the art having regard to the type of formulation in question, for example those suitable for oral administration may include flavouring agents.

In the above-described methods of treatment and uses, a compound of formula (I) may be employed alone, in combination with one or more other compounds of formula (I) or in combination with other therapeutic agents. Thus, the present invention also encompasses pharmaceutical compositions further comprising one or more therapeutic agents. In one embodiment, the pharmaceutical compositions further comprise a vaccine. Examples of other therapeutic agents include, but are not limited to TLR3 agonists, TLR4 agonists, or other innate immunity receptor agonists, for example nucleotide oligomerization domain (NOD) agonists, retinoic acid-inducible gene (RIG) agonists and stimulator of interferon genes (STING) agonists. A compound of formula (I) may be further employed with a metal salt such as an aluminium salt.

The methods and uses employing these combinations may comprise the administration of the compound of formula (I) and another therapeutic agent simultaneously in separate or combined pharmaceutical compositions. When combined in the same composition it will be appreciated that the compounds must be stable and compatible with each other and the other components of the composition and may be formulated for administration. When formulated separately they may be provided in any convenient formulation, in such a manner as are known for such compounds in the art.

When a compound of formula (I) is used in combination with another therapeutic agent, the dose of each compound may differ from that when the compound is used alone. Appropriate doses will be readily appreciated by those skilled in the art. The appropriate dose of the compound(s) of formula (I) and the other therapeutically active agent(s) and the relative timings of administration will be selected in order to achieve the desired combined therapeutic effect, and are within the expertise and discretion of the attendant clinician.

Compounds of the invention can be made according to any suitable method of organic chemistry.

Further, it will be apparent to those skilled in the art that certain reaction steps may be most efficiently performed by installing protecting groups prior to the reaction, which are removed subsequently. The choice of protecting groups as well as general techniques for their installation and removal are within the skill of those in the art. It will be appreciated by those skilled in the art that certain ring systems represented in the generic ring structure will require the use of a protective group to minimize the possibility of undesired side reactions from occurring. The protective group may be easily installed by methods contained in the literature and likewise may be removed once they are no longer needed.

According to one method, a compound of formula (I) may be prepared using the process depicted in Scheme 1, below.

Scheme 1

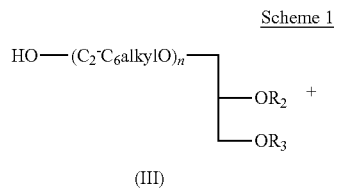

(III)

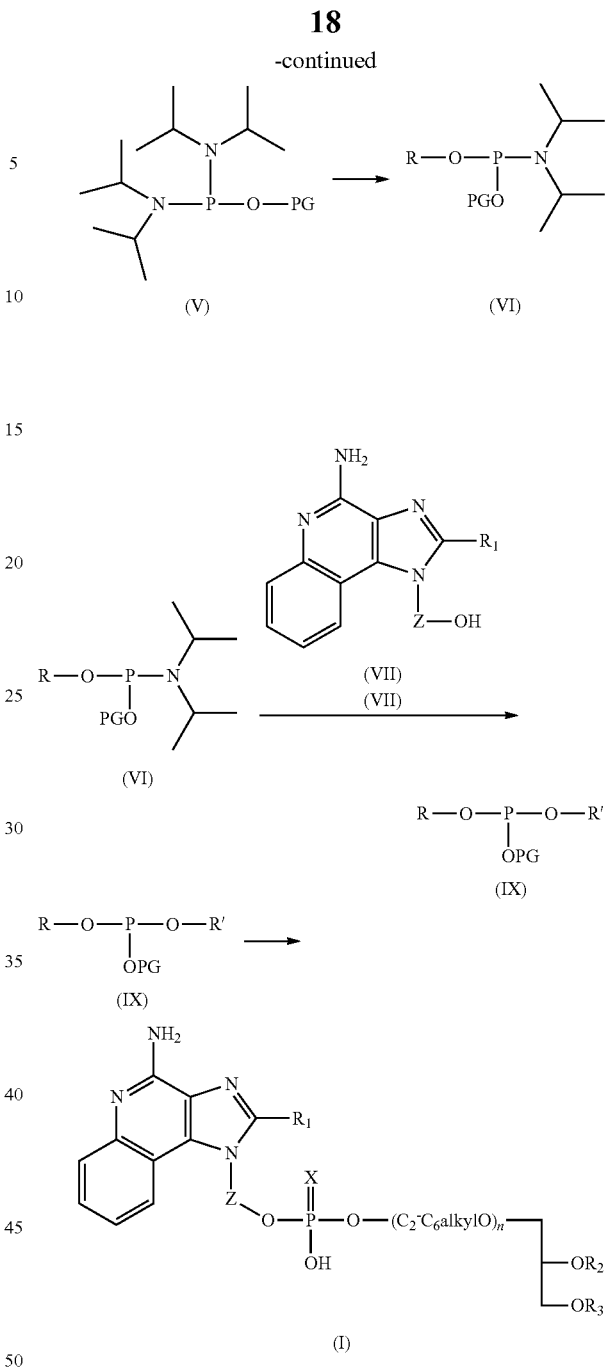

wherein

PG is a protecting group suitable for hydroxyl protection, including but not limited to cyanoethyl, methyl, ethyl, benzyl and allyl group;

R is

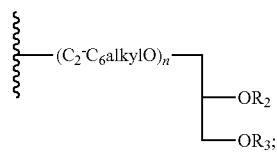

R' is

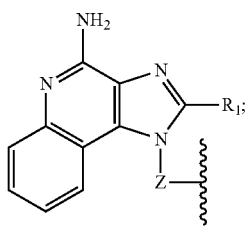

all other variables are as defined above for formula (I).

In general, the process for preparing a compound of formula (I) as depicted in Scheme 1 comprises the steps of:

a) reacting a compound of formula (III) with a compound of formula (V) to prepare a compound of formula (VI);

b) reacting a compound of formula (VI) with a compound of formula (VII) to to prepare a compound of formula (IX); and c) oxidizing a compound of formula (IX) and removing the hydroxyl protecting group to obtain a compound of formula (I);

d) optionally converting the compound of formula (I) into a pharmaceutically acceptable salt thereof;

e) optionally converting the compound of formula (I) into a different compound of formula (I).

Scheme 2

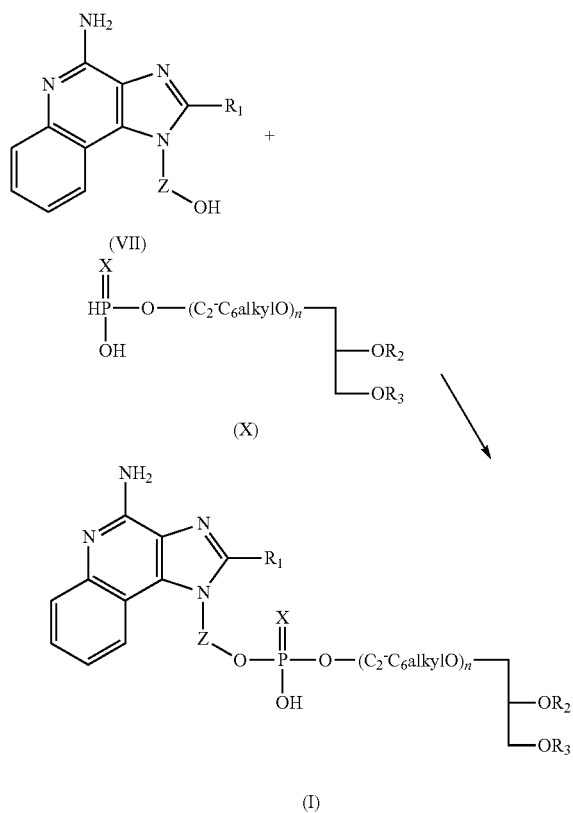

wherein $R_1$ is selected from H, $C_{1-6}$alkyl, $C_{1-6}$alkylamino, $C_{1-6}$alkoxy, $C_{3-6}$cycloalkyl$C_{1-6}$alkyl, $C_{3-6}$cycloalkyl$C_{1-6}$alkylamino, $C_{3-6}$cycloalkyl$C_{1-6}$alkoxy, $C_{1-6}$alkoxy$C_{1-6}$alkyl, $C_{1-6}$alkoxy$C_{1-6}$alkylamino and $C_{1-6}$alkoxy$C_{1-6}$alkoxy; wherein the $C_{1-6}$alkyl, $C_{1-6}$alkylamino, $C_{1-6}$alkoxy, $C_{3-6}$cycloalkyl$C_{1-6}$alkyl, $C_{3-6}$cycloalkyl$C_{1-6}$alkylamino, $C_{3-6}$cycloalkyl$C_{1-6}$alkoxy, $C_{1-6}$alkoxy$C_{1-6}$alkyl, $C_{1-6}$alkoxy$C_{1-6}$alkylamino or $C_{1-6}$alkoxy$C_{1-6}$alkoxy is branched or unbranched and optionally terminally substituted with a hydroxyl, amino, thio, hydrazino, hydrazido, azido, acetylenyl, carboxyl, or maleimido group;

Z is selected from $C_2$-$C_6$ alkyl and $C_2$-$C_6$ alkenyl, wherein the $C_2$-$C_6$ alkyl or $C_2$-$C_6$ alkenyl is unsubstituted or terminally substituted by —(O—$C_2$-$C_6$alkyl)$_{1-6}$-;

X is O or S;

$R_2$ is H or a straight or branched, optionally unsaturated, $C_4$-$C_{24}$ alkyl, or a straight or branched, optionally unsaturated, $C_4$-$C_{24}$, acyl;

$R_3$ is a straight or branched, optionally unsaturated, $C_4$-$C_{24}$ alkyl or a straight or branched, optionally unsaturated, $C_4$-$C_{24}$ acyl.

n is 1, 2, 3, 4, 5, 6, 7, 8, 9, 10, 11, 12, 13, 14, 15, 16, 17, 18, 19 or 20.

In another aspect, the present invention provides another process for preparing a compound of formula (I). This process comprises the steps of:

a) reacting a compound of formula (VII) with a H-phosphonate compound of formula (X) to form a compound of formula (I);

b) optionally converting the compound of formula (I) into a pharmaceutically acceptable salt thereof;

c) optionally converting the compound of formula (I) into a different compound of formula (I).

In one embodiment, a compound of formula (I) may be prepared according to Scheme 2 wherein step a) utilizes methods described in Crossman, et al. *J Chem Soc, Perkin Trans I*, 1997, 2769, Westerduin, et. al. *Tet Lett*, 1986, 15, 6271; or Nikolaev, et al., *Carbohydr Res*, 1990, 204, 65.

Based upon these examples and the disclosure contained herein one skilled in the art can readily convert compounds of formula (I) into other compounds of formula (I), or salts thereof.

The following examples are intended for illustration only and are not intended to limit the scope of the invention in any way, the present invention being defined by the claims.

In the examples, the following terms have the designated meaning:

eq=equivalents;

ES TOF-MS=electrospray time of flight mass spectroscopy;

h=hour;

H=hydrogen atom;

Hz=Hertz; mHz=megaHertz;

LC-MS: liquid chromatography-mass spectroscopy;

min=minute;

ml=milliliter;

M=molar;

NMR=nuclear magnetic resonance;

rt=room temperature;

TEA=triethylamine;

µg=microgram;

µl=microliter;

v=volume.

Example 1

General Procedure for the Synthesis of Compound of Formula (I)

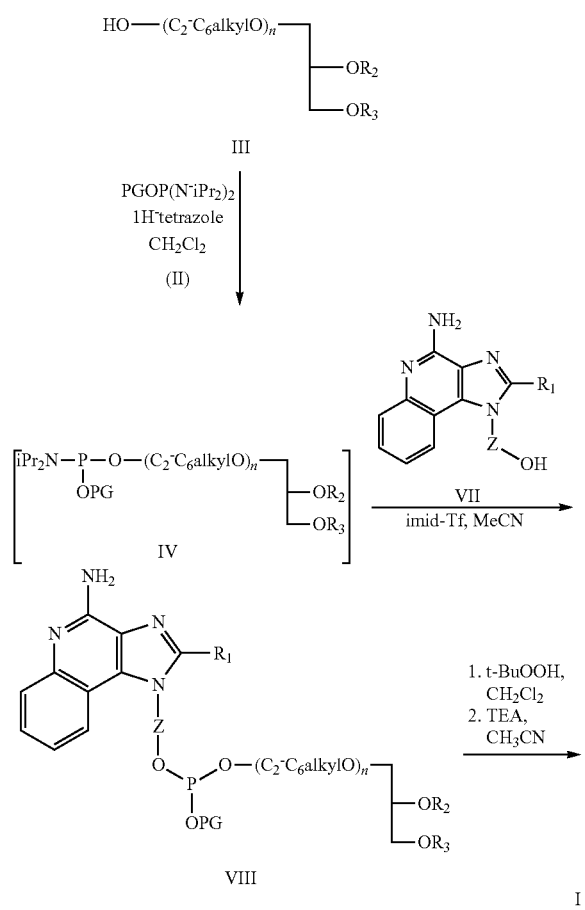

Imidazoquinoline monophosphate glycerides (I) were prepared by
a) reacting a compound of formula (III) (prepared according to methods known in the art, *Bioorg Med Chem*, 2013, 21, 3066; *ChemBioChem*, 2012, 13, 2331; *Chem Eur* 2006, 6, 111), with a phosphordiamidite reagent of formula (II) (commercially available) according to methods known in the art;
b) reacting a compound of formula (IV) (not isolated) in-situ with an imidazoquinoline of formula (VII) (Gerster et al., *J Med. Chem.*, 2005, 48, 3481; Izumi et al., *Bioorg Med Chem*, 2003, 11, 2541) according to methods known in the art;
c) oxidizing a compound of formula (VIII) and removing the protecting group according to methods known in the art to produce a compound of formula (I).

A compound of formula (III) (2.0 eq) and 2-cyanoethyl N,N,N',N'-tetraisopropylphosphordiamidite of formula (II) (2.1 eq) were dissolved in anhydrous methylene chloride (0.4 M) at rt. 1H-tetrazole (2.1 eq) was added in four portions over 20 min and the reaction mixture stirred at rt for 1 h. The reaction mixture was cooled to 0° C., imidazoquinoline of formula (VII) (1.0 eq) and imidazolium triflate (1.5 eq) were added, and the reaction mixture allowed to warm up to rt. The reaction was usually completed after 1 h at rt. The resulting phosphite of formula (VIII) can be purified at this stage (after reducing the volume by concentration under vacuum) or subsequently oxidized by addition of t-butyl hydroperoxide (1.5 eq) to the reaction mixture and stirring at rt for 30 min. After completion of the oxidation, the reaction mixture was concentrated under vacuum and purified by chromatography on silica gel. The resulting protected phosphotriester was dissolved in acetonitrile (0.06 M). Triethylamine (acetonitrile:TEA 1:0.35 v:v) was added and the reaction mixture stirred at rt for 6 to 18 h. Once the deprotection was complete, the reaction mixture was filtered over a Büchner filter and the isolated solid rinsed with acetonitrile and dried under high vacuum, or purified by chromatography on silica gel.

Example 2

Synthesis of 4-amino-1-[2-(1,2-dipalmitoyl-sn-glycero-3-ethyleneglycol-phospho)ethyl]-2-n-butyl-1H-imidazo[4,5-c]quinoline. Designated Compound 2 in HEK293 Results

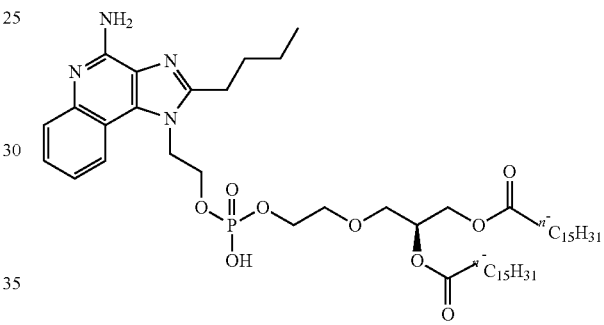

4-amino-1-[2-(1,2-dipalmitoyl-sn-glycero-3-ethyleneglycol-phospho)ethyl]-2-n-butyl-1H-imidazo[4,5-c]quinoline was prepared in 66% yield following the general procedure described in Example 1. $^1$H NMR (400 MHz, CDCl$_3$/CD$_3$OD) δ 8.19 (bs, 1H), 7.38 (s, 1H), 7.13 (bs, 1H), 6.93 (bs, 1H), 5.24 (s, 1H), 4.83 (bs, 2H), 4.58 (bs, 2H), 4.39 (dd, 1H), 4.17 (m, 1H), 4.02 (dd, 2H), 3.68 (m, 4H), 2.98 (bs, 2H), 2.31 (dd, 4H), 1.93 (bs, 2H), 1.58 (m, 2H), 1.25 (m, 48H), 1.03 (t, 3H), 0.86 (t, 6H); negative ES TOF-MS calc for [M−H]$^-$ 957.6445, found 957.6414.

Example 3

Synthesis of 4-amino-1-[2-(1,2-dipalmitoyl-sn-glycero-3 triethyleneglycol-phospho)ethyl]-2-n-butyl-1H-imidazo[4,5-c]quinoline Designated Compound 3 in HEK293 Results

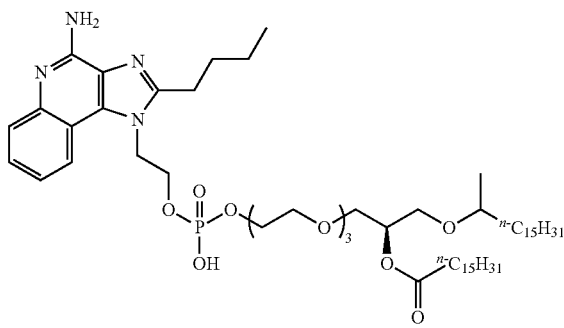

4-amino-1-[2-(1,2-dipalmitoyl-sn-glycero-3 triethyleneglycol-phospho)ethyl]-2-n-butyl-1H-imidazo[4,5-c]quinoline was prepared in 62% yield following the general procedure described in example 1. $^1$H NMR (400 MHz, CDCl$_3$/CD$_3$OD) δ 8.23 (d, 1H), 7.42 (t, 1H), 7.20 (t, 1H), 6.97 (t, 1H), 5.23 (m, 1H), 4.74 (bd, 2H), 4.63 (bd, 2H), 4.34 (dd, 1H), 4.15 (dd, 1H), 4.05 (m, 2H), 3.58-3.71 (m, 12H), 3.04 (bt, 2H), 2.31 (dd, 4H), 1.92 (m, 2H), 1.52-1.59 (m, 6H), 1.26 (m, 48H), 1.04 (t, 3H), 0.88 (t, 6H); negative ES TOF-MS calc for [M−H]$^-$ 1045.6970, found 1045.6855.

Example 4

Synthesis of 4-amino-1-[2-(1,2-dipalmitoyl-sn-glycero-3 hexaethyleneglycol-phospho)ethyl]-2-n-butyl-1H-imidazo[4,5-c]quinoline Designated Compound 4 in HEK293 Results

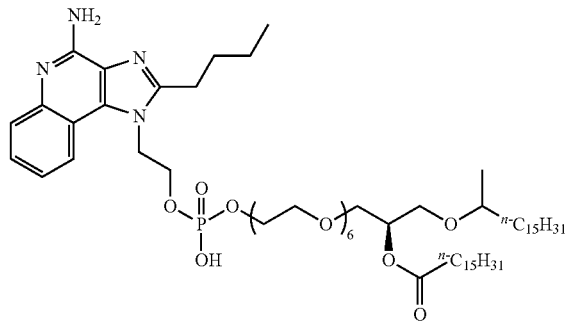

4-amino-1-[2-(1,2-dipalmitoyl-sn-glycero-3 hexaethyleneglycol-phospho)ethyl]-2-n-butyl-1H-imidazo[4,5-c]quinoline was prepared in 76% yield following the general procedure described in example 1. $^1$H NMR (400 MHz, CDCl$_3$/CD$_3$OD) δ 8.18 (bs, 1H), 7.36 (t, 1H), 7.18 (bs, 1H), 6.97 (bs, 1H), 5.20 (m, 1H), 4.67 (bs, 2H), 4.33 (dd, 1H), 4.15 (dd, 1H), 4.06 (m, 2H), 3.57-3.71 (m, 26H), 3.01 (bs, 2H), 2.31 (dd, 4H), 1.93 (m, 2H), 1.52-1.61 (m, 6H), 1.25 (m, 48H), 1.04 (t, 3H), 0.87 (t, 6H); negative ES TOF-MS calc for [M−H]$^-$ 1177.7756, found 1177.9063.

Example 5

Synthesis of 4-amino-1-[2-(1,2-dipalmitoyl-sn-glycero-3 nonaethyleneglycol-phospho)ethyl]-2-n-butyl-1H-imidazo[4,5-c]quinoline Designated Compound 5 in HEK293 Results

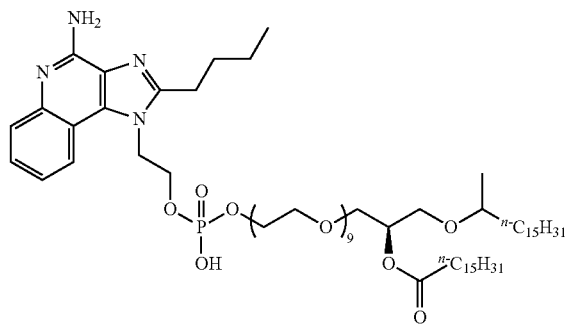

4-amino-1-[2-(1,2-dipalmitoyl-sn-glycero-3 nonaethyleneglycol-phospho)ethyl]-2-n-butyl-1H-imidazo[4,5-c]quinoline was prepared in 53% yield following the general procedure described in example 1. $^1$H NMR (400 MHz, CDCl$_3$/CD$_3$OD) δ 8.19 (bs, 1H), 7.40 (t, 1H), 7.19 (bs, 1H), 6.96 (bs, 1H), 5.23 (m, 1H), 4.50-4.80 (bm, 4H), 4.35 (dd, 1H), 4.16 (dd, 1H), 4.03 (bs, 2H), 3.58-3.71 (m, 33H), 3.03 (bs, 2H), 2.84 (m, 2H), 2.30 (dd, 4H), 1.93 (m, 2H), 1.52-1.63 (m, 6H), 1.25 (m, 48H), 1.04 (t, 3H), 0.88 (t, 6H); negative ES TOF-MS calc for [M−H]$^-$ 1309.8543, found 1310.0106.

Example 6

HEK293 Binding Assay

Determination of TLR agonist activity was performed using the HEK293 binding assay. This assay measures TLR7 and TLR8 selectivity and potency of the compounds tested. HEK293 cells expressing human TLR7 or TLR8 and NFκB responsive Secreted Embryonic Alkaline Phosphatase (SEAP) reporter gene were obtained from InvivoGen (San Diego, Calif.). These cells were maintained in culture media of Dulbecco's Modified Eagle Medium (DMEM) (Invitrogen, Grand Island, N.Y.), 10% Fetal Bovine Serum (FBS) (Sigma, St. Louis, Mo.) and selection antibiotics (Invitrogen, and Invivogen). HEK293 stably transfected with human TLR7 (hTLR7) or human TLR8 (hTLR8) were stimulated for 24 h with aqueous formulations of compounds and culture supernatants were analyzed for NFκB activation using the colorimetric SEAP detection kit QuantBlue (InvivoGen).

Compounds 2, 3, 4 and 5 are as described above. Compound 1 is 4-amino-1-[2-(1,2-dipalmitoyl-sn-glycero-3-phospho)ethyl]-2-n-butyl-1H-imidazo[4,5-c]quinoline. It is included although it is not a PEGylated derivative to show the increase of TLR7/8 activity and cytokine induction when introducing a PEGylated moiety into Compound 1. The results of the HEK293 binding assay are shown in FIG. 1A and FIG. 1B and summarized in Table 1.

TABLE 1

| Compound | 1 | 2 | 3 | 4 | 5 |
|---|---|---|---|---|---|
| TLR7 ED50 | 38.8 | 1.8 | 1.4 | 3.4 | 24.0 |
| TLR8 ED50 | 13.1 | 8.7 | 1.4 | 7.8 | 19.2 |
| TLR7/8 Ratio | 3.0 | 0.2 | 1.0 | 0.4 | 1.3 |

Example 7

Assay to Measure Cytokine Induction

PEGylated analogs were evaluated for cytokine induction in human peripheral blood mononuclear cells (hPBMCs).
Preparation of hPBMCs
Primary human PBMCs were isolated from fresh blood from healthy donors via Ficoll gradient separation and plated at 0.5×10$^6$ cells/well in 96-well tissue culture plates (RPMI-1640 plus 10% FBS). hPBMCs were maintained with RPMI-1640 culture media (Invitrogen, Grand Island, N.Y.), antibiotics (Invitrogen) and 10% FBS (Sigma).
Incubation and Assays for Interferon-Alpha and TNF-Alpha
hPBMCs were stimulated for 24 h with aqueous formulations of Compounds 1-5. Culture supernatants were analyzed for TNF-α induction using multiplex kits (FluoroKine

The invention claimed is:

1. A compound, or a pharmaceutically acceptable salt thereof, of formula (I):

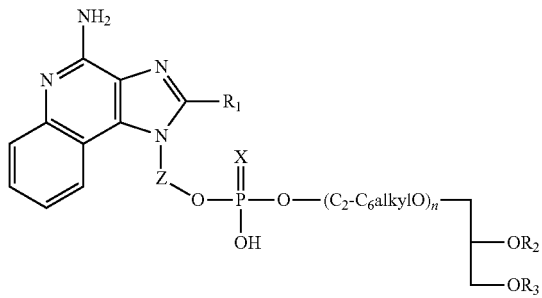

(I)

wherein $R_1$ is selected from H, $C_{1-6}$alkyl, $C_{1-6}$alkylamino, $C_{1-6}$alkoxy, $C_{3-6}$cycloalkyl$C_{1-6}$alkyl, $C_{3-6}$cycloalkyl$C_{1-6}$alkylamino, $C_{3-6}$cycloalkyl$C_{1-6}$alkoxy, $C_{1-6}$alkoxy$C_{1-6}$alkyl, $C_{1-6}$alkoxy$C_{1-6}$alkylamino and $C_{1-6}$alkoxy$C_{1-6}$alkoxy; wherein the $C_{1-6}$alkyl, $C_{1-6}$alkylamino, $C_{1-6}$alkoxy, $C_{3-6}$cycloalkyl$C_{1-6}$alkyl, $C_{3-6}$cycloalkyl$C_{1-6}$alkylamino, $C_{3-6}$cycloalkyl$C_{1-6}$alkoxy, $C_{1-6}$alkoxy$C_{1-6}$alkyl, $C_{1-6}$alkoxy$C_{1-6}$alkylamino or $C_{1-6}$alkoxy$C_{1-6}$alkoxy is branched or unbranched and optionally terminally substituted with a hydroxyl, amino, thio, hydrazino, hydrazido, azido, acetylenyl, carboxyl, or maleimido group;

Z is selected from $C_2$-$C_6$ alkyl and $C_2$-$C_6$ alkenyl, wherein the $C_2$-$C_6$ alkyl or $C_2$-$C_6$ alkenyl is unsubstituted or terminally substituted by —(O—$C_2$-$C_6$alkyl)$_{1-6}$-;

X is O or S;

n is 1, 2, 3, 4, 5, 6, 7, 8, 9, 10, 11, 12, 13, 14, 15, 16, 17, 18, 19 or 20;

$R_2$ is H or a straight or branched, optionally unsaturated, $C_4$-$C_{24}$ alkyl, or a straight or branched, optionally unsaturated, $C_4$-$C_{24}$, acyl;

$R_3$ is a straight or branched, optionally unsaturated, $C_4$-$C_{24}$ alkyl or a straight or branched, optionally unsaturated, $C_4$-$C_{24}$ acyl.

2. The compound or pharmaceutically acceptable salt according to claim 1 wherein $R_1$ is selected from H, $C_{1-6}$alkyl, $C_{1-6}$alkylamino and $C_{1-6}$alkoxy wherein the $C_{1-6}$alkyl, $C_{1-6}$alkylamino or $C_{1-6}$alkoxy is branched or unbranched and optionally terminally substituted with a hydroxyl, amino, thio, hydrazino, hydrazido, azido, acetylenyl, carboxyl, or maleimido group.

3. The compound or pharmaceutically acceptable salt according to claim 1 wherein $R_1$ is n-butyl.

4. The compound or pharmaceutically acceptable salt of claim 1 wherein Z is $(CH_2)_2$.

5. The compound or pharmaceutically acceptable salt of claim 1 wherein X is O.

6. The compound or pharmaceutically acceptable salt of claim 1 wherein n is selected from 3 or 6.

7. The compound or pharmaceutically acceptable salt of claim 1 wherein $R_2$ is a straight or branched, optionally unsaturated, $C_4$-$C_{24}$ acyl.

8. The compound or pharmaceutically acceptable salt of claim 1 wherein $R_3$ is a straight or branched, optionally unsaturated, $C_4$-$C_{24}$ acyl.

9. The compound or pharmaceutically acceptable salt of claim 1 wherein $R_2$ is unbranched $C_{16}$ acyl (palmitoyl, $COC_{15}H_{31}$).

10. The compound or pharmaceutically acceptable salt of claim 1 wherein $R_3$ is unbranched $C_{16}$ acyl (palmitoyl, $COC_{15}H_{31}$).

11. The compound of claim 1 wherein $R_1$=n-butyl; Z is $(CH_2)_2$; n is selected from 3, 6 and 9; $R_2$ is unbranched $C_{16}$ acyl (palmitoyl, $COC_{15}H_{31}$) and $R_3$ is unbranched $C_{16}$ acyl (palmitoyl, $COC_{15}H_{31}$).

12. A pharmaceutical composition comprising a compound according to claim 1 and a pharmaceutically acceptable carrier or diluent.

* * * * *